United States Patent
Han et al.

(10) Patent No.: US 11,040,333 B2
(45) Date of Patent: *Jun. 22, 2021

(54) METHOD FOR PREPARING DEHYDROGENATION CATALYST FOR STRAIGHT CHAIN-TYPE LIGHT HYDROCARBON USING STABILIZED ACTIVE MATERIAL COMPLEX

(71) Applicant: HEESUNG CATALYSTS CORPORATION, Gyeonggi-do (KR)

(72) Inventors: Hyun-sik Han, Seoul (KR); Young-san Yoo, Gyeonggi-do (KR); Ho-Dong Kim, Gyeonggi-do (KR); Dong Kun Kang, Gyeonggi-do (KR)

(73) Assignee: HEESUNG CATALYSTS CORPORATION, Gyeonggi-do (KR)

( * ) Notice: Subject to any disclaimer, the term of this patent is extended or adjusted under 35 U.S.C. 154(b) by 135 days.

This patent is subject to a terminal disclaimer.

(21) Appl. No.: 15/774,140

(22) PCT Filed: Oct. 31, 2016

(86) PCT No.: PCT/KR2016/012353
§ 371 (c)(1),
(2) Date: May 7, 2018

(87) PCT Pub. No.: WO2017/082565
PCT Pub. Date: May 18, 2017

(65) Prior Publication Data
US 2018/0311644 A1   Nov. 1, 2018

(30) Foreign Application Priority Data

Nov. 10, 2015  (KR) .................. 10-2015-0157393

(51) Int. Cl.
*B01J 23/62* (2006.01)
*B01J 37/02* (2006.01)
(Continued)

(52) U.S. Cl.
CPC ............. *B01J 23/626* (2013.01); *B01J 23/62* (2013.01); *B01J 23/624* (2013.01);
(Continued)

(58) Field of Classification Search
CPC ........ B01J 23/626; B01J 23/62; B01J 23/624; B01J 23/6562; B01J 35/0066;
(Continued)

(56) References Cited

U.S. PATENT DOCUMENTS 4,077,912 A   3/1978 Dolhyj et al.
4,255,253 A   3/1981 Herrington et al.
(Continued)

FOREIGN PATENT DOCUMENTS

KR   10-2010-0078465 A   7/2010
KR   10-2014-0006909 A   1/2014
(Continued)

OTHER PUBLICATIONS

Zangeneh et al. (The influence of solvent on the performance of Pt-Sn/theta-Al2O3 propane dehydrogenation catalyst prepared by co-impregnation method, 2013, Fuel processing Technology, 109, pp. 118-123) (Year: 2013).*
(Continued)

*Primary Examiner* — Patricia L. Hailey
(74) *Attorney, Agent, or Firm* — Ballard Spahr LLP

(57) ABSTRACT

The present invention relates to a catalyst having improved selectivity and reactivity and applied to preparing olefins by dehydrogenating C9 to C13 paraffin, and particularly to a technique for preparing a catalyst, which uses a heat-treated support having controlled pores, and most of metal compo-
(Continued)

nents contained therein are distributed evenly in a support in the form of an alloy rather than in the form of each separate metal, thereby exhibiting high a conversion rate and selectivity when used in dehydrogenation.

7 Claims, 3 Drawing Sheets

(51) Int. Cl.
*B01J 35/10* (2006.01)
*B01J 23/656* (2006.01)
*B01J 35/00* (2006.01)
*B01J 37/00* (2006.01)
*B01J 35/02* (2006.01)
*B01J 35/08* (2006.01)
*C07C 5/333* (2006.01)
*B01J 31/02* (2006.01)
*B01J 37/08* (2006.01)
*B01J 37/18* (2006.01)

(52) U.S. Cl.
CPC ......... *B01J 23/6562* (2013.01); *B01J 35/008* (2013.01); *B01J 35/0066* (2013.01); *B01J 35/023* (2013.01); *B01J 35/026* (2013.01); *B01J 35/08* (2013.01); *B01J 35/109* (2013.01); *B01J 35/1061* (2013.01); *B01J 35/1066* (2013.01); *B01J 35/1076* (2013.01); *B01J 37/0018* (2013.01); *B01J 37/0203* (2013.01); *B01J 37/0213* (2013.01); *C07C 5/3337* (2013.01); *B01J 31/0202* (2013.01); *B01J 35/0093* (2013.01); *B01J 37/0207* (2013.01); *B01J 37/088* (2013.01); *B01J 37/18* (2013.01); *B01J 2523/00* (2013.01); *C07C 2523/62* (2013.01)

(58) Field of Classification Search
CPC ...... B01J 35/008; B01J 35/023; B01J 35/026; B01J 35/08; B01J 35/1061; B01J 35/1066; B01J 35/1076; B01J 35/109; B01J 37/0018; B01J 37/0203; B01J 37/0213; B01J 31/0202; B01J 35/0093; B01J 37/0207; B01J 37/088; B01J 37/18; B01J 2523/00; C07C 5/3337; C07C 2523/62; C22C 5/04; C22C 13/00

USPC ......... 502/325, 330; 585/616, 654; 420/466, 420/557

See application file for complete search history.

(56) References Cited

U.S. PATENT DOCUMENTS

| | | |
|---|---|---|
| 4,716,143 A | 12/1987 | Imai |
| 4,786,625 A | 11/1988 | Imai et al. |
| 6,177,381 B1 | 1/2001 | Jensen et al. |
| 8,993,474 B2 | 3/2015 | Choi et al. |
| 2007/0123418 A1* | 5/2007 | Han ........................ B01J 23/63 502/339 |
| 2009/0275792 A1* | 11/2009 | Vogel ..................... B01J 23/626 585/660 |
| 2013/0261363 A1* | 10/2013 | Serban ..................... B01J 23/63 585/430 |
| 2014/0323785 A1* | 10/2014 | Lande ................... C07C 5/3337 585/660 |
| 2015/0158024 A1* | 6/2015 | Lande ..................... B01J 23/58 585/660 |
| 2018/0311645 A1* | 11/2018 | Han ........................ B01J 21/04 |

FOREIGN PATENT DOCUMENTS

| | | |
|---|---|---|
| KR | 10-1527841 B1 | 6/2015 |
| WO | WO-2012/101567 A2 | 8/2012 |
| WO | WO-2017/082564 A1 | 5/2017 |

OTHER PUBLICATIONS

Wang, X. et al., Pt/Sn Intermettalic, Core/Shell and Alloy Nanoparticles: Colloidal Synthesis and Structural Control. Chem Mater. 2013; 25:1400-7.

Zangeneh, F.T. et al., The Influence of Solvent on the Performance of Pt—Sn/θ-$Al_2O_3$ Propane Dehydrogenation Catalyst Prepared by Co-Impregnation Method. Fuel Process Technol. 2013; 109:118-23.

International Search Report dated Feb. 14, 2017 by the International Searching Authority for Patent Application No. PCT/KR2016/012353, which was filed on Oct. 31, 2016 and published as WO 2017/082565 on May 18, 2017 (Inventor—Han et al.; Applicant—Heesung Catalysts Corp.) (Translation Only—2 pages).

International Search Report dated Feb. 14, 2017 by the International Searching Authority for Patent Application No. PCT/KR2016/012352, which was filed on Oct. 31, 2016 and published as WO 2017/082564 on May 18, 2017 (Inventor—Han et al.; Applicant—Heesung Catalysts Corp.) (Translation Only—2 pages).

* cited by examiner

[FIG. 1]
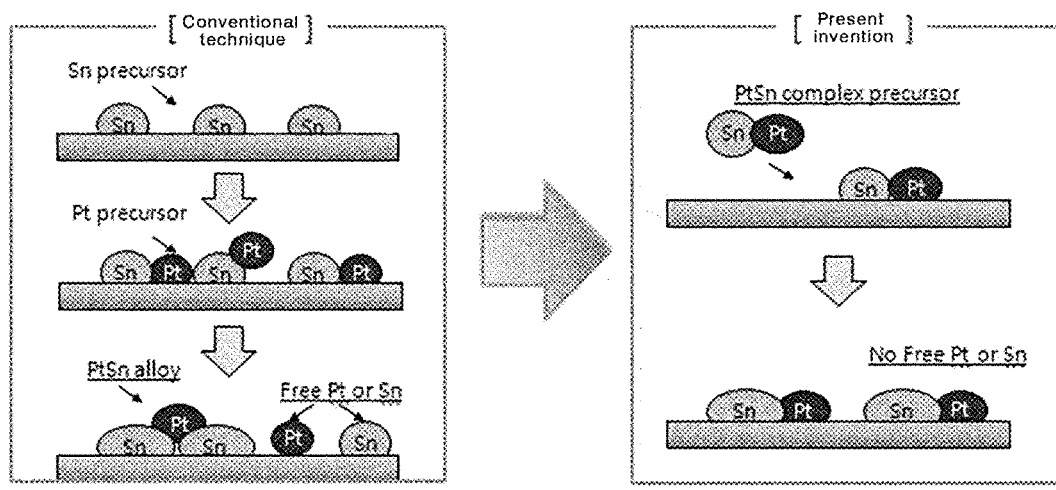
[FIG. 2]
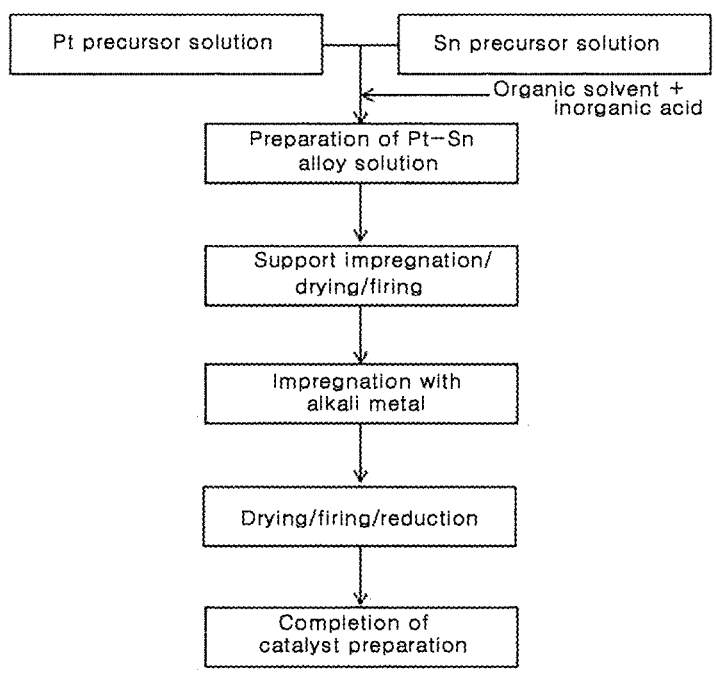

[FIG. 3]
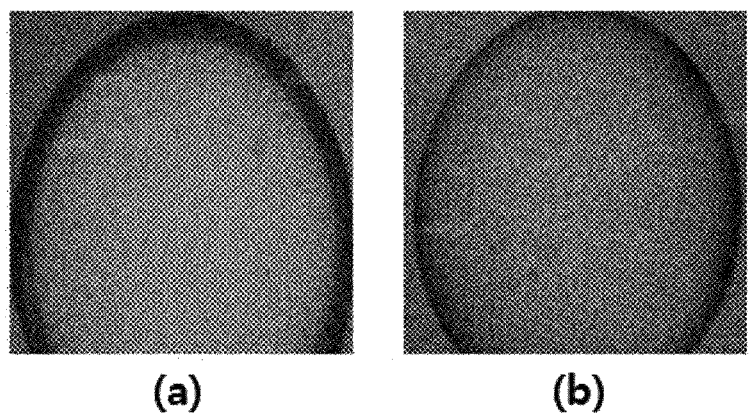
(a)          (b)
[FIG. 4]
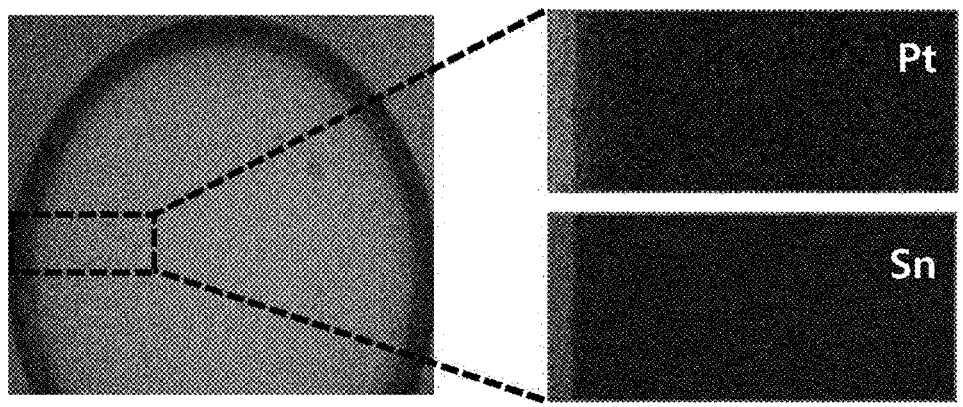

[FIG. 5]
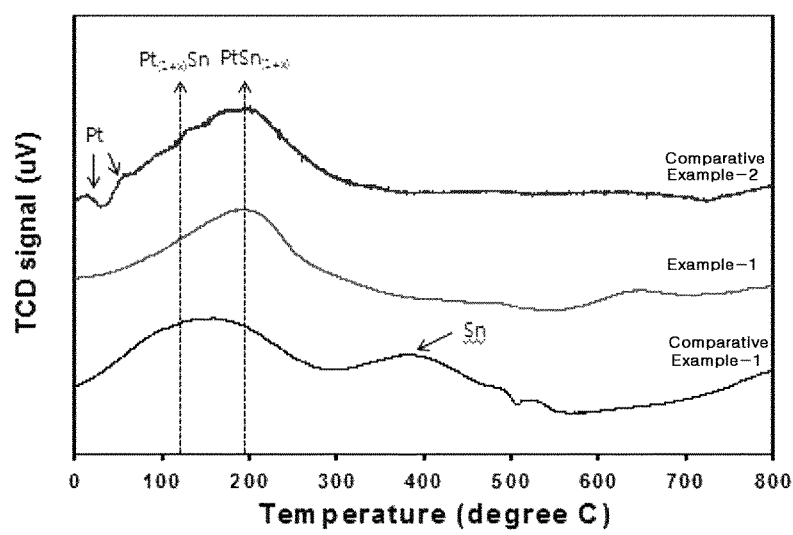

METHOD FOR PREPARING DEHYDROGENATION CATALYST FOR STRAIGHT CHAIN-TYPE LIGHT HYDROCARBON USING STABILIZED ACTIVE MATERIAL COMPLEX

CROSS-REFERENCE TO RELATED APPLICATIONS

This application is a U.S. National Phase Application of International Application No. PCT/KR2016/012353, filed Oct. 31, 2016, which claims priority to Korean Application No. 10-2015-0157393, filed Nov. 10, 2015, each of which are hereby incorporated by reference in their entirety.

TECHNICAL FIELD

The present invention relates to a catalyst that exhibits improved selectivity and reactivity, suitable for use in the preparation of an olefin by dehydrogenating $C_9$~$C_{13}$ paraffin, and more particularly to a technique for preparing a catalyst configured such that a thermally treated support having controlled pores is used and most metal components contained in the catalyst are uniformly distributed not in the form of individual metals but in the form of an alloy in a support from the outer surface of the catalyst support, thus exhibiting a high conversion rate and selectivity when used for dehydrogenation. In particular, in the preparation of the catalyst, an organic solvent is used in order to support a metal, whereby distribution of individual metals in the catalyst is suppressed, thus increasing an intermetallic alloying rate, and also, a dispersion stabilizer is used to thereby increase the extent of dispersion of active metals.

BACKGROUND ART

Typically, a linear olefin having 9 or more carbon atoms, which is to be dehydrogenated, is a highly economical compound that is widely utilized as a basic material for intermediates for preparing biodegradable detergents, medicines, plastics, synthetic rubber and the like. Methods of producing linear olefin from linear paraffin having 9 to 13 or more carbon atoms through dehydrogenation are known, and generally include bringing hydrogen and gaseous paraffin into contact with a dehydrogenation catalyst, followed by reaction at a high temperature under atmospheric pressure. In the dehydrogenation reaction system, the catalyst has been prepared to mainly increase the rate of reaction and simultaneously inhibit side reactions such as pyrolysis, coke production, isomerization, etc. so as to increase linear olefin selectivity.

A dehydrogenation catalyst, which is commonly useful for producing linear olefin from linear paraffin, is mainly prepared by supporting a Group VIII noble metal such as platinum or the like on silica, gamma/theta/eta alumina, silica-alumina, zeolite, etc. Such a catalyst is problematic because metal particles may be sintered early due to the high temperature in the initial stage of the reaction, undesirably shortening the lifetime of the catalyst. In order to prevent the deterioration of the activity of the catalyst for dehydrogenating linear paraffin, the olefin selectivity, and the catalytic activity due to carbon deposition, useful is a catalyst configured such that a Group VIII noble metal is coupled with one or more other metals selected from among tin, lithium, potassium, sodium, etc. Meanwhile, in the reaction mechanism for dehydrogenating a paraffinic hydrocarbon, the reaction progresses at a high temperature, and thus, not only the dehydrogenation reaction but also side reactions such as pyrolysis and coke production may occur, undesirably lowering catalytic activity and selectivity. Particularly in the case of a catalyst configured such that the active metal is deeply incorporated into the support, total dispersibility becomes good, and thus even when the reactant is incorporated into the support through material transfer and diffusion, it comes into contact with the metal active sites, thus increasing the total activity. However, the reactant or product may reside in the catalyst for an excessively long period of time, undesirably causing side reactions such as adsorption of the product inside the catalyst, additional reaction of products, isomerization and coke production, and shortening the lifetime of the catalyst. Hence, thorough research is ongoing into active metal distribution in the support to suppress side reactions in the dehydrogenation reaction and to increase the produced olefin selectivity. In particular, there are proposed methods for disposing the active metal on the outer surface of the catalyst support to decrease the material transfer effect, and to increase the selectivity and maximize the activity by suppressing additional dehydrogenation due to the chain reaction by minimizing the contact time between the reactant or the product and the catalyst.

For example, U.S. Pat. Nos. 4,077,912 and 4,255,253 disclose a catalyst prepared by coating a support with a catalytic metal oxide, thus enabling incorporation to the outer surface of the support, and U.S. Pat. No. 6,177,381 discloses a catalyst where, in order to prevent the diffusion of an active metal into the support upon loading of the active metal, alpha alumina and cordierite are used as the inner core, and gamma alumina and active metal are mixed to give a slurry which is then used to form an outer layer, thereby increasing the selectivity and the extent of dehydrogenation using the catalyst. The above patent also discloses that the slurry for forming the outer layer is mixed together with the active metal, after which the resulting mixture may be applied on the inner core, or alternatively that the slurry may be applied and the active metal may then be loaded thereon.

DISCLOSURE

Technical Problem

However, such a multilayered catalyst having a core-shell configuration is problematic because the core and the shell are separately manufactured, and thus the manufacturing process is complicated, and also because the density of the support is increased due to the use of the fired alpha alumina or cordierite as the support, and high manufacturing costs may result. Furthermore, the slurry for the shell is unfavorable in that interlayer loss may occur upon friction in the catalyst, compared to monolithic spherical support catalysts. Although an organic or inorganic binder is used to attach the inner core and the outer layer in the manufacture of the multilayered catalyst, the organic binder for preventing the outer layer from being stripped may decrease the surface area of the outer layer due to thermal impact resulting from heat of the dehydrogenation reaction, and the inorganic binder may decrease the number of reaction active sites on the outer layer. Typically, platinum, which provides active sites for the dehydrogenation reaction, and tin, which improves platinum stability, have to be present in the form of an alloy, but the conventional technique is problematic because platinum and tin are sequentially supported, and thus the platinum-tin alloy form depends only on the contact probability of the two active materials, and the alloy having the optimal platinum/tin molar ratio for a desired reaction may be present together with platinum alone or other alloys having different platinum/tin molar ratios, so side reactions occur during the reaction.

Technical Solution

The present invention provides a dehydrogenation catalyst for a paraffinic hydrocarbon, which is structurally stable by directly supporting active metals to a support, rather than in the form of a typical shell-core-type multilayer structure, and also in which active metals are not present alone in the support but are maintained uniform in the form of an alloy, thereby significantly increasing the olefin conversion rate and selectivity, and also provides a method of preparing the same. In addition, the present invention provides a catalyst, in which platinum as an active material and tin as an auxiliary metal are allowed to be present in a complex form at a desired tin/platinum molar ratio using an organic solvent from an initial impregnation step and an organic stabilizer is added in order to enhance the extent of dispersion to thus prepare a precursor solution, which is then used to impregnate the support. Here, the catalyst is able to control the thickness/distribution of the active metal layer from the outer surface of the support to the inside thereof by adjusting the surface properties of alumina depending on the ratio of inorganic acid and organic solvent in the active material distribution layer.

Advantageous Effects

According to the present invention, the catalyst is configured such that platinum and tin have a consistent distribution in the support, and platinum and tin are present in the form of an alloy having a consistent platinum/tin molar ratio by reduction. Therefore, improved selectivity can result from minimizing platinum alone, tin alone, and other alloys having different platinum/tin molar ratios. Depending on the composition of the mixed organic solvent, it is possible to control the thickness of the platinum-tin complex in the catalyst, whereby the optimal active metal distribution can be controlled in response to the form of the reactant. Since the active metal is supported to the support itself, stripping of the active material can be suppressed and the catalyst of the invention is remarkably improved in durability due to high strength, compared to conventional catalysts, and is thus economically superior.

DESCRIPTION OF DRAWINGS

FIG. 1 shows the key process of the present invention compared to a conventional technique;

FIG. 2 is a flowchart showing the processing steps of the present invention;

FIG. 3 shows video microscopy images of catalysts prepared by adjusting the thickness of active metal in Example 2 according to the present invention and Comparative Example 1;

FIG. 4 shows a video microscopy image (a) of the catalyst prepared using a thermally treated support in Example 2 according to the present invention and electron probe microanalysis (EPMA) images (b) thereof; and FIG. 5 shows the state of alloying of active metals using H2-TPR (Hydrogen Temperature-Programmed Reduction) of the catalysts of Example 1 and Comparative Examples 1 and 2.

BEST MODE

The present invention relates to a catalyst exhibiting improved selectivity and reactivity, suitable for use in the preparation of olefin by dehydrogenating C9-C13 paraffin, and the present inventors have ascertained that the use of a catalyst prepared by intensively supporting active metals only to the outer surface of a support may suppress the dehydrogenation side reaction and may also improve the conversion rate and selectivity upon the catalytic reaction. Particularly, it has been confirmed that when mono-olefin as the target product is prepared from a C9 or higher hydrocarbon having a large molecular size, high selectivity may be expected due to the active material distribution on the outer surface of the support. FIG. 1 shows the key process of the present invention compared to the conventional technique, and FIG. 2 shows the flowchart of the process of the present invention. The method of the present invention as shown in FIG. 2 is comprehensively described below.

1) Preparation of Stabilized Platinum-Tin Complex Solution

A platinum-tin complex solution enables the easy precipitation of platinum in air due to the high reducibility of tin. In the preparation of a complex solution, the selection of a solvent is very important. When water is used as the solvent, platinum is reduced by tin and thus the platinum-tin precursor solution becomes very unstable, and consequently platinum particles may precipitate, and thus the use thereof as the precursor is impossible. In the present invention, the precursor solution is made stable over time using a solvent that may prevent tin reduction. Specifically, during the mixing of platinum and tin precursors, these precursors are added to an organic solvent so as not to break a platinum-tin complex, and a dispersion stabilizer is added to thus prepare a solution in which the particles are not aggregated. As the organic solvent and dispersion stabilizer, any one or two selected from among water, methanol, ethanol, butanol, acetone, ethyl acetate, acetonitrile, ethylene glycol, triethylene glycol, glycol ether, glycerol, sorbitol, xylitol, dialkyl ether, and tetrahydrofuran may be sequentially used, or may be used in combination. During the preparation of the platinum-tin complex solution, aging in an inert gas atmosphere is performed to thus suppress decomposition by oxygen and realize stabilization. Here, the inert gas may include nitrogen, argon, and helium, and preferably nitrogen gas.

2) Preparation of Catalyst Using Stabilized Platinum-Tin Complex Solution and Alkali Metal A PtSn complex solution in an amount corresponding to the total pore volume of the support is prepared, and is used to impregnate the support using a spraying process. After the impregnation process, the catalyst is homogenized while the catalyst is allowed to flow in a nitrogen atmosphere, whereby the active metal concentrations on the surface of the catalyst are made the same, followed by drying at 100 to 150° C. for 24 hr. After the drying, the organic material is removed at 200 to 400° C. in a nitrogen atmosphere, followed by firing at 400 to 700° C. in air. If thermal treatment is carried out at a temperature of less than 400° C., the supported metal may not change into metal oxide species. On the other hand, if thermal treatment is carried out at a temperature of higher than 700° C., intermetallic aggregation may occur, and the activity of the catalyst is not high relative to the amount thereof. After the firing, in order to suppress side reactions of the catalyst, the loading of an alkali metal is carried out. Specifically, lithium is loaded to the pores in the support using the same spraying process as in the platinum-tin complex solution, dried at 100 to 150° C. for 24 hr, and then fired at 400 to 700° C. in air. Finally, after the firing, a reduction process is carried out at 400 to 600° C. using a hydrogen/nitrogen mixed gas (4%/96% 100%/0%), thereby yielding a catalyst. During the reduction process, if the reduction temperature is lower than 400° C., metal oxide species cannot be completely reduced, and two or more kinds of metal particles may be individually present, rather than in the form of an alloy. On the other hand, if the reduction temperature is higher than 600° C., aggregation and sintering of two or more kinds of metal particles may occur, whereby the incidence of active sites may decrease and catalytic activity may be lowered. The reduction process is carried out not in a heating reduction manner with hydrogen gas from a heating step, but in a high-temperature reduction manner in which a nitrogen atmosphere is maintained until the temperature reaches the corresponding temperature, after which hydrogen gas is introduced at the corresponding temperature.

3) Evaluation of Catalyst Performance

A method of converting a paraffin hydrocarbon into an olefin may be conducted in a manner in which the dehydrogenation catalyst according to the present invention is used, and a hydrocarbon having 2 to 20 carbon atoms, and preferably 9 to 13 carbon atoms, including paraffin, iso-paraffin, and alkyl aromatic material, is diluted with hydrogen, and may then be subjected to a gaseous reaction at 400~600° C., preferably 470° C., 0~2 atm, preferably 1.6 atm, and a LHSV (Liquid Hourly Space Velocity) of a paraffin hydrocarbon of 1~30 h$^{-1}$, and preferably 20~30 h$^{-1}$. The reactor for producing olefin through dehydrogenation is not particularly limited, and a fixed-bed catalytic reactor in which the catalyst is packed may be used. Also, since the dehydrogenation reaction is endothermic, it is important that the catalytic reactor be maintained adiabatic at all times. The dehydrogenation reaction of the present invention should be carried out under conditions in which the reaction temperature, pressure and liquid space velocity are maintained within appropriate ranges. If the reaction temperature is low, the reaction does not occur, and if the reaction temperature is too high, the reaction pressure increases in proportion thereto, and moreover, side reactions, such as coke production, isomerization, and the like, may occur.

Example 1

The support of Example 1 was used after pore control of a gamma-alumina support (made by BASF, Germany, specific surface area: 210 m$^2$/g, pore volume: 0.7 cm$^3$/g, average pore size: 8.5 nm) through firing at 800° C. for 5 hr. The thermally treated alumina had physical properties including a specific surface area of 150 m$^2$/g, a pore volume of 0.6 cm$^3$/g, and an average pore size of 10 nm, and had a dual pore structure comprising mesopores of 10 nm or less and macropores of 50 μm or more. A platinum precursor, chloroplatinic acid ($H_2PtCl_6$), and a tin precursor, tin chloride ($SnCl_2$), were used, and chloroplatinic acid in an amount of 0.2 wt % based on the total weight of the catalyst and tin chloride at a tin/platinum molar ratio of 1.0 were mixed in a nitrogen atmosphere. Next, the platinum-tin mixture was added to a solvent in an amount corresponding to the total pore volume of the support and thus dissolved. The solvent comprising ethanol/ethylene glycol/hydrochloric acid at a weight ratio of 100:20:1.5 was used. The support was impregnated with the prepared platinum-tin complex solution using an incipient wetness process. The platinum-tin-supported composition was thermally treated at 600° C. in air for 4 hr to thus immobilize active metals. Thereafter, 0.6 wt % of lithium nitride ($Li(NO_3)_2$) based on the total weight of the catalyst was supported to the pores in the support using an incipient wetness process, and the metal-supported composition was thermally treated at 400° C. in air, thereby preparing a metal-supported catalyst. The catalyst was reduced stepwise in a manner in which the temperature was elevated to 400° C. in a nitrogen atmosphere and then maintained for 4 hr using a hydrogen/nitrogen mixed gas (4%/96%), thereby preparing a catalyst. This catalyst was configured such that platinum and tin were distributed at a thickness of 120 μm on the outer surface of the support and lithium was uniformly distributed in the support.

Example 2

The catalyst of Example 2 was prepared in the same manner as in Example 1, with the exception that the tin/platinum molar ratio was changed to 2.0 upon the preparation of the tin-platinum complex solution. This catalyst was configured such that platinum and tin were distributed at a thickness of 120 μm on the outer surface of the support and lithium was uniformly distributed in the support.

Example 3

The catalyst of Example 3 was prepared in the same manner as in Example 1, with the exception that the tin/platinum molar ratio was changed to 3.0 upon the preparation of the tin-platinum complex solution. This catalyst was configured such that platinum and tin were distributed at a thickness of 120 μm on the outer surface of the support and lithium was uniformly distributed in the support.

Example 4

The catalyst of Example 4 was prepared in the same manner as in Example 1, with the exception that the tin/platinum molar ratio was changed to 4.0 upon the preparation of the tin-platinum complex solution. This catalyst was configured such that platinum and tin were distributed at a thickness of 120 μm on the outer surface of the support and lithium was uniformly distributed in the support.

Example 5

The catalyst of Example 5 was prepared in the same manner as in Example 2, with the exception that the solvent comprising ethanol/ethylene glycol/hydrochloric acid at a weight ratio of 100:20:1.0 was used upon the preparation of the platinum-tin complex solution. This catalyst was configured such that platinum and tin were distributed at a thickness of 60 μm on the outer surface of the support and lithium was uniformly distributed in the support.

Example 6

The catalyst of Example 6 was prepared in the same manner as in Example 2, with the exception that the solvent comprising ethanol/ethylene glycol/hydrochloric acid at a weight ratio of 100:20:2.5 was used upon the preparation of the platinum-tin complex solution. This catalyst was configured such that platinum and tin were distributed at a thickness of 250 μm on the outer surface of the support and lithium was uniformly distributed in the support.

Comparative Example 1

In accordance with the method disclosed in U.S. Pat. No. 4,786,625, a catalyst was prepared. A tin-containing gamma-alumina (made by SASOL, Germany) support was impregnated through an incipient wetness process after dilution of 0.2 wt % of chloroplatinic acid and 0.6 wt % of lithium nitride and thiomalic acid, based on the total weight of the catalyst, with deionized water in an amount corresponding to the total pore volume of the alumina support. Thereafter, the solvent was evaporated at 80° C. using an evaporation dryer, followed by thermal treatment at 540° C. for 4 hr to thus immobilize active metals. Thereafter, a reduction reaction was carried out in a hydrogen atmosphere at 540° C. for 4 hr, thus preparing a catalyst. This catalyst was configured such that platinum was mostly distributed at a thickness of 60 µm on the outer surface of the support but some of the platinum was present up to 150 µm in the support, and tin was distributed at a thickness of 200 µm on the outer surface of the support, and tin and lithium were uniformly distributed in the support.

Comparative Example 2

In accordance with the method disclosed in U.S. Pat. No. 4,716,143, a catalyst was prepared. A thermally treated gamma-alumina support (having a specific surface area of 150 m²/g, a pore volume of 0.6 cm³/g, and an average pore size of 10 nm) was impregnated through an incipient wetness process after dilution of chloroplatinic acid in an amount of 0.2 wt % based on the total weight of the catalyst, tin chloride at a tin/platinum molar ratio of 2.0 and hydrochloric acid in an amount of 0.5 wt % based on the total weight of the catalyst with deionized water in an amount corresponding to the total pore volume of the alumina support. The support was impregnated with the prepared platinum-tin complex solution using an incipient wetness process. The platinum-tin-supported composition was dried at 150° C. for 24 hr and then thermally treated at 540° C. in air for 4 hr to thus immobilize active metals. Thereafter, 0.6 wt % of lithium nitride based on the total weight of the catalyst was supported to the pores in the support through an incipient wetness process, and the metal-supported composition was thermally treated at 540° C. in air, thereby preparing a metal-supported catalyst. The catalyst was reduced at 540° C. in a hydrogen atmosphere for 4 hr, thus obtaining a catalyst. This catalyst was configured such that platinum was mostly distributed at a thickness of 180 µm on the outer surface of the support but some of the platinum was present up to 400 µm in the support, and tin was distributed at a thickness of 200 µm on the outer surface of the support, and lithium was uniformly distributed in the support.

Comparative Example 3

The catalyst of Comparative Example 3 was prepared in the same manner as in Comparative Example 2, with the exception that, upon the supporting of platinum and tin, the solvent was added with hydrochloric acid in an amount of 2.0 wt % based on the total weight of the catalyst. This catalyst was configured such that platinum, tin and lithium were uniformly distributed in the support.

The active metal distribution properties in the catalysts of Examples and Comparative Examples are shown in Table 1 below.

Test Examples 1 to 9: Evaluation of Catalyst Performance

In order to measure the activity of the catalyst, a dehydrogenation reaction was carried out, and a fixed-bed reaction system was used as a reactor. Specifically, 1.16 g of the catalyst was placed in a tube-shaped reactor, and hydrogen gas was allowed to uniformly flow at a rate of 235 cc/min so that the catalyst was reduced at 470° C. for 1 hr. Subsequently, the temperature of the reactor was uniformly maintained at 470° C., after which a paraffin hydrocarbon feed having 9 to 13 carbon atoms was continuously supplied into the reactor at a constant rate of 0.7 ml/min using an HPLC pump, and the liquid space velocity was set to 21 $h^{-1}$. The reaction pressure was maintained at 1.6 atm using a pressure regulator. The material produced after the reaction was cooled to a temperature of 4° C. or less and stored, and the product taken out of the reactor was transferred to a gas chromatograph through a line wound with a thermal line, and quantitative analysis was performed using an FID (Flame Ionization Detector) and a TCD (Thermal Conductivity Detector). The paraffin conversion rate and olefin selectivity of the product were calculated based on the following equations. The properties of the products using the above catalysts are summarized in Table 2 below.

Paraffin conversion rate=[paraffin mol before reaction−paraffin mol after reaction]/[paraffin mol before reaction]×100

Olefin selectivity=[olefin mol in product]/[product mol]×100%.

FIG. 3 shows video microscopy images of the catalysts prepared by adjusting the thickness of the active metal in Example 2 according to the present invention and in Comparative Example 1. Specifically, the image of (a) shows the catalyst of Example 2 using the tin-platinum alloy solution, and the image of (b) shows the catalyst of Comparative Example 1 using individual platinum and tin solutions. FIG. 4 shows a video microscopy image (a) of the catalyst prepared using the thermally treated support in Example 2 according to the present invention and the electron probe microanalysis (EPMA) images (b) thereof. As shown in the images of (b), platinum and tin of the cross-section of the catalyst were distributed at a uniform thickness in the catalyst. FIG. 5 shows the state of alloying of the active metals using H2-TPR (Hydrogen Temperature-Programmed Reduction) in the catalysts of Example 1 and Comparative Examples 1 and 2. In Example 1, Pt and Sn were not present alone, and only the peak of a PtSn alloy was observed, unlike Comparative Examples 1 and 2.

TABLE 1

| No. | Sn/Pt molar ratio | Metal distribution in support | Thickness of metal layer from outer surface of support (µm) | | Pt-Sn dispersibility (%) |
|---|---|---|---|---|---|
| | | | Pt | Sn | |
| Example 1 | 1 | Uniform | 120 | 120 | 60 |
| Example 2 | 2 | Uniform | 120 | 120 | 58 |
| Example 3 | 3 | Uniform | 120 | 120 | 57 |
| Example 4 | 4 | Uniform | 120 | 120 | 52 |
| Example 5 | 2 | Uniform | 60 | 60 | 53 |
| Example 6 | 2 | Uniform | 250 | 250 | 55 |
| Comparative Example 1 | 2 | Non-uniform | 60-100 | 1400 | 48 |
| Comparative Example 2 | 2 | Non-uniform | 180, 400 | 200 | 50 |
| Comparative Example 3 | 2 | Uniform | 1400 | 1400 | 55 |

TABLE 2

| No. | Catalyst | Paraffin conversion rate (%) 4 h/24 h | Mono-olefin selectivity (%) 4 h/24 h | Di-olefin selectivity (%) 4 h/24 h | Olefin yield (%) 4 h/24 h |
|---|---|---|---|---|---|
| Test Example 1 | Example 1 | 19.0/18.1 | 88.5/87.8 | 7.9/7.8 | 18.3/17.3 |
| Test Example 2 | Example 2 | 19.1/18.9 | 89.8/89.9 | 8.1/8.2 | 18.7/18.5 |
| Test Example 3 | Example 3 | 18.7/18.6 | 89.8/89.8 | 8.0/8.0 | 18.3/18.2 |
| Test Example 4 | Example 4 | 18.4/18.3 | 90.1/90.1 | 8.1/8.2 | 18.1/18.0 |
| Test Example 5 | Example 5 | 18.6/18.4 | 89.9/89.9 | 8.3/8.2 | 18.3/18.1 |
| Test Example 6 | Example 6 | 19.1/18.7 | 82.7/82.1 | 8.4/7.9 | 17.4/16.8 |
| Test Example 7 | Comparative Example 1 | 18.9/18.2 | 88.8/88.5 | 7.9/7.8 | 18.3/17.5 |
| Test Example 8 | Comparative Example 2 | 18.5/17.9 | 81.0/79.8 | 8.0/7.8 | 16.5/15.7 |
| Test Example 9 | Comparative Example 3 | 19.6/18.9 | 78.4/74.1 | 7.7/6.9 | 16.8/15.3 |

CONCLUSION

When the tin/platinum molar ratio is equal to or less than a predetermined level, the amount of tin preventing deactivation due to coke is small around platinum and thus initial reaction activity may increase but rapid deactivation occurs, undesirably deteriorating durability. On the other hand, when the tin/platinum molar ratio is equal to or greater than a predetermined level, some of the platinum active sites are covered with tin to thus increase selectivity, but the total activity may decrease, ultimately lowering the olefin yield. When the metal layer is thin, a TOF (Turn-Over Frequency) with which the reactant passes through the catalyst is lowered and thus the overall paraffin conversion rate is slightly decreased, but the produced olefin compounds have short retention time in the catalyst and thus pass through the catalyst without side reactions, thereby increasing the olefin yield. In contrast, when the metal layer is thick, the retention time of the reactant in the catalyst active layer is increased, thus raising the conversion rate. However, while the reactant passes through the catalyst, primary dehydrogenation occurs, after which re-adsorption in the catalyst, secondary dehydrogenation, isomerization, cracking, and polymerization take place sequentially, thus decreasing the olefin selectivity, resulting in lowered olefin yield. In Comparative Examples 1 and 2, platinum is not uniformly distributed in the support, and thus an overall non-uniform reaction is carried out, and because of platinum particles present alone and particles having a low tin-platinum alloy ratio in the catalyst, the paraffin conversion rate is increased upon catalytic reaction, but side reactions such as cracking occur, undesirably decreasing olefin selectivity. The product is transferred to platinum particles alone or platinum containing a small amount of tin due to side reactions to thus block active sites, thus causing rapid deactivation of the catalyst, resulting in low durability. Based on the reaction results of Examples and Comparative Examples, the catalyst exhibiting the optimal conversion rate, selectivity and durability is determined to be the catalyst of Example 2, in which the molar ratio of uniform tin-platinum alloy is 2 and the thickness of the metal layer is about 110 to 130 µm.

The invention claimed is:

1. A dehydrogenation catalyst for use in dehydrogenation of a hydrocarbon gas containing 9 to 13 carbon atoms, configured such that platinum, tin, and an alkali metal are supported to an alumina having controlled pores, wherein the platinum and the tin are in the form of an alloy at a consistent platinum/tin molar ratio at a thickness in an egg-shell shape from the outer surface of the alumina from 110 µm to 250 µm, and wherein the alkali metal is uniformly distributed within the alumina.

2. The dehydrogenation catalyst of claim 1, wherein the platinum/tin molar ratio is 2.0-4.0.

3. The dehydrogenation catalyst of claim 1, wherein the alumina is spherical.

4. The dehydrogenation catalyst of claim 1, wherein the catalyst is configured such that, based on a total weight of the catalyst, 0.1-1.0 wt % of the platinum, 0.2-4.0 wt % of the tin, and 0.1-3.0 wt % of the alkali metal are supported to the alumina.

5. The dehydrogenation catalyst of claim 1, wherein the alkali metal is at least one selected from the group consisting of potassium, sodium, and lithium.

6. A method of dehydrogenating a hydrocarbon, comprising bringing a hydrocarbon gas into contact with the catalyst of claim 1 under dehydrogenation conditions.

7. The method of claim 6, wherein the hydrocarbon gas includes a hydrocarbon gas containing 9 to 13 carbon atoms suitable for dehydrogenation.

* * * * *